(12) United States Patent
Hansis et al.

(10) Patent No.: US 8,923,474 B2
(45) Date of Patent: Dec. 30, 2014

(54) VISUALIZATION OF THE CORONARY ARTERY TREE

(75) Inventors: Eberhard Sebastian Hansis, Menlo Park, CA (US); Michael Grass, Buchholz In Der Nordheide, DC (US)

(73) Assignee: Koninklijke Philips N.V., Eindhoven (NL)

( * ) Notice: Subject to any disclaimer, the term of this patent is extended or adjusted under 35 U.S.C. 154(b) by 451 days.

(21) Appl. No.: 13/131,277

(22) PCT Filed: Nov. 20, 2009

(86) PCT No.: PCT/IB2009/055220
§ 371 (c)(1),
(2), (4) Date: Jul. 28, 2011

(87) PCT Pub. No.: WO2010/061328
PCT Pub. Date: Jun. 3, 2010

(65) Prior Publication Data
US 2012/0020462 A1    Jan. 26, 2012

(30) Foreign Application Priority Data
Nov. 26, 2008   (EP) ...................................... 08169941

(51) Int. Cl.
*G01N 23/083*   (2006.01)
*A61B 6/00*   (2006.01)
*G06T 11/00*   (2006.01)

(52) U.S. Cl.
CPC ............... *A61B 6/504* (2013.01); *A61B 6/4441* (2013.01); *A61B 6/466* (2013.01); *A61B 6/481* (2013.01); *G06T 11/006* (2013.01); *G06T 2211/404* (2013.01); *A61B 6/541* (2013.01)
USPC ..................... 378/4; 378/19; 378/95; 382/131

(58) Field of Classification Search
CPC ... G06T 11/003; G06T 11/005; G06T 11/008; G06T 15/06; G06T 15/08; G06T 15/205; G06T 2211/40; G06T 2211/404; G06T 2211/412; A61B 6/03; A61B 6/032; A61B 6/4441; A61B 6/461; A61B 6/466; A61B 6/481; A61B 6/486; A61B 6/503; A61B 6/504; A61B 6/507; A61B 6/5211; A61B 6/5217; A61B 6/5264; A61B 6/527; A61B 6/5288
USPC .............. 378/4, 8, 19, 95, 901; 382/128, 131, 382/130
See application file for complete search history.

(56) References Cited

U.S. PATENT DOCUMENTS 5,459,769 A  *  10/1995  Brown ............................... 378/4
5,687,208 A  *  11/1997  Bae et al. .......................... 378/8
(Continued)

FOREIGN PATENT DOCUMENTS

WO   2009077978 A1   6/2009

*Primary Examiner* — Thomas R Artman (57) ABSTRACT

The present invention is related to a method for reconstruction of the coronary arteries and an examination apparatus for reconstruction of the coronary arteries. To provide improved coronary artery information, an apparatus and a method are provided where a gating signal is provided (32) and a first gated X-ray image sequence of one of the left or right branches of the coronary arteries is acquired (34) with injected contrast agent into the one of the left or right branches of the coronary arteries. Further, a second gated X-ray image sequence of the other branch of the coronary arteries is acquired (36) with injected contrast agent into said other branch. Then, a gated reconstructing (38) of the left and the right coronary artery is suggested and a volume data (40, 42) of the coronary arteries is generated. The volume data of the left and right coronary arteries is registered (44) in relation to time and space. Further; the registered volume data (48, 50) of the left and the right coronary arteries is combined and a combined coronary artery tree volume data set (52) is generated (54). Finally, the combined coronary tree volume data set is visualized (56).

23 Claims, 6 Drawing Sheets

(56) References Cited

U.S. PATENT DOCUMENTS

| | | | |
|---|---|---|---|
| 5,797,396 A * | 8/1998 | Geiser et al. | 600/407 |
| 6,154,518 A * | 11/2000 | Gupta | 378/62 |
| 6,501,848 B1 | 12/2002 | Carroll et al. | |
| 6,718,004 B2 | 4/2004 | Cesmeli | |
| 7,113,623 B2 | 9/2006 | Chen et al. | |
| 7,180,976 B2 | 2/2007 | Wink et al. | |
| 2003/0002616 A1 * | 1/2003 | Cesmeli | 378/8 |
| 2003/0069499 A1 | 4/2003 | Lienard et al. | |
| 2004/0066958 A1 * | 4/2004 | Chen et al. | 382/128 |
| 2005/0096522 A1 * | 5/2005 | Reddy et al. | 600/407 |
| 2006/0083415 A1 * | 4/2006 | El Fakhri et al. | 382/128 |
| 2006/0245536 A1 * | 11/2006 | Boing et al. | 378/8 |
| 2006/0253017 A1 * | 11/2006 | O'Donnell et al. | 600/410 |
| 2006/0293579 A1 | 12/2006 | Schmitt et al. | |
| 2008/0253634 A1 * | 10/2008 | Hay et al. | 382/130 |
| 2008/0253638 A1 * | 10/2008 | Binkley et al. | 382/131 |
| 2010/0278405 A1 * | 11/2010 | Kakadiaris et al. | 382/131 |

* cited by examiner

VISUALIZATION OF THE CORONARY ARTERY TREE

FIELD OF THE INVENTION

The present invention is related to a method for reconstruction of the coronary arteries and an examination apparatus for reconstruction of the coronary arteries.

BACKGROUND OF THE INVENTION

During interventions, for diagnosis purposes, treatment planning or outcome control of an intervention, it is known to visualise the left and right coronary arteries partly surrounding the heart by using X-ray image generating devices of the so-called C-type. The visualisation is usually based on a reconstruction of the coronary arteries by the means of at least two acquired images. For acquisition, the left or the right branch of the coronary arteries (LCA or RCA) are selectively injected with a contrast agent. In other words, images are acquired for the left branch separately from the acquisition of the images of the right branch. Usually the acquisitions are analysed independently for a diagnosis on the whole coronary artery tree. But it has shown that this provides inadequate information to the user, i.e., for example, a surgeon or cardiologist. However, a need may exist to provide comprehensive information about the current coronary artery situation.

SUMMARY OF THE INVENTION

The present invention aims at providing improved coronary artery information.

The object may be reached with an examination apparatus for reconstruction of the coronary arteries and a method for reconstruction of the coronary arteries, according to the independent claims.

In an exemplary embodiment, a method is provided that comprises the following steps.

First, a gating signal is provided. Then a first gated X-ray image sequence of one of the left or right branches of the coronary arteries is acquired with injected contrast agent into the one of the left or right branches of the coronary arteries. Further, a second gated X-ray image sequence of the other branch of the coronary arteries is acquired with injected contrast agent to said other branch. Then the left and the right coronary arteries are reconstructed and volume data of the coronary arteries is generated. The volume data of the left and right coronary arteries is temporally registered. The volume data of the left and right coronary arteries is also spatially registered. The registered volume data of the left and the right coronary arteries is then combined and a combined coronary artery tree volume data set is generated. Finally, the combined coronary tree volume data set is visualised.

The volume data set comprises for example a three-dimensional voxel data set. It is also possible that the volume data set comprises an extracted model, for example with rendered surfaces or centrelines. According to the invention, the volume data set can also comprise additional information such as a relation to time, which will be described below in relation with another embodiment. In other words, the combined coronary tree volume data set is providing information about both the left branch of the coronary arteries and the right branch of the coronary arteries. Viewing the whole coronary artery tree potentially simplifies the assessment of the coronary artery geometry by showing all coronary arteries in three-dimensional view at once. This provides the user, for example, a cardiac surgeon or a cardiologist, with a widespread knowledge about the cardiac situation of the patient. As an exemplary application, the present invention allows for an assessment of total occlusions within the coronary arteries. When separately acquiring only one half of the artery tree, i.e. when acquiring only the left or the right branch, such an occlusion within a coronary artery only results in a non-visible artery volume, because the volume behind the occlusion is not filled with a contrast agent during the image acquisition. According to the invention, in case of an occluded vessel, a retrograde filling from the respective other branch will take place during the acquisition procedure. Thereby it is possible to reveal the location of otherwise invisible occluded vessels. The joint visualisation of the right coronary artery and the left coronary artery then shows the vessel both before and after the occlusion.

The term gated acquisition stands, for example, for a continuous acquisition where a temporal reference signal is provided to allow for retrospective gating. The images are selected after the completion of the continuous acquisition sequence, for example by relating the projections to cardiac phases by providing an electrocardiogram as the gating signal. It is also possible to accomplish a prospective gating, but this reduces the possibilities to reconstruct all cardiac phases from one acquisition.

It is to be noted that the above-described method has the visual effect that both sides of the artery tree of the same cardiac cycle are displayed. In other words, the artery tree branches have the same direct relation on the display as they have in the currently observed object, e.g. a patient. That means, the inventive method can easily be detected by the generated image being displayed.

Once both branches of the coronary arteries have been registered, according to a preferred embodiment, the information can also be displayed with additional information from other sources, such as the combined display with coronary veins or other arteries.

According to an exemplary embodiment, the first and the second gated X-ray image sequences are rotational coronary angiography image sequences.

This provides improved acquisition data for the reconstruction procedural steps.

In an exemplary embodiment, the reconstruction is a tomographical reconstruction.

This provides detailed information about the coronary artery tree branches, which also provides the visualisation of rather thin and small furcations, in other words, this allows for a visualisation of the complete branches. Hence, the information provided to the user allows for far better analysis of the patient's situation.

In an exemplary embodiment, a combined coronary artery tree volume data set is generated for each cardiac phase, wherein each cardiac phase is temporally registered in relation to the gating signal.

Thus, visually understandable information is provided for the different cardiac phases and provides the information necessary for complete analysis of the coronary artery situation.

In another exemplary embodiment, at least one combined coronary artery tree film sequence is generated.

By generating a film sequence, dynamic information about the heart motion can be provided. For example, the film sequence can be displayed to impart the user, e.g. a surgeon, with an easier understanding of the situation.

In a further exemplary embodiment of the method, the displacement amount of the left and right artery is determined. Then the determined displacement values are converted into visual values. Further, the displacement amount is displayed.

By providing a time series of the inventive combined reconstructions, a basis is established for further dynamic analysis procedures of the heart. By providing the displacement information in a visual way, i.e. the displacement values are encoded into visual aspects, such as brightness or colour, respectively different greyscales, the information can very easily be recognised by the user.

In a further exemplary embodiment, the speed of a displacement of the left and right arteries is determined by relating the displacement values to time. The determined speed values are then converted into visual values. Then the speed occurrences can be displayed on a display.

This provides the user with further information concerning the motion of the heart. This is possible, because the coronary artery tree largely encloses the heart. Therefore, the motion of the combined coronary artery tree is a good indicator of the heart motion itself. For example, by providing the displacement values and/or the speed values of the displacement, information is provided that assists the detection of abnormal motion of the heart which, as a result, allows for an improved diagnosis by, for example, a cardiologist.

In a further exemplary embodiment, the method also comprises the steps of determining the displacement of the left and right arteries in relation to each other and comparing the displacement with preset displacement values. Then the displacement information is generated and displayed on a display.

This allows for an automatic detection of, for example, an abnormal motion of the heart. For example, the displacement information may include a signal that a displacement has occurred that exceeded the preset displacement values. Further, it is also possible to display information about the frequency of occurrence of said exceeding displacement values. By providing such exceedance information the user is given a first indication that a closer examination may be necessary. In other words, the user can detect at a glance if certain displacement values have been exceeded or not. In case the exceeding information is present, he can then look closer on further displacement information such as the maximum displacement or the maximum speed of the displacement.

According to the invention, the different aspects are displayed together on a display. For example, the coronary tree volume data set or model image is displayed within a major part of the display. The other aspects, according to the aforementioned exemplary embodiments, can be displayed on smaller parts of the display, for example, surrounding the display part showing the combined coronary tree volume data set, e.g. a model image. In case the user is interested in the further information given on the smaller parts of the display, by entering a respective command into an interface unit, the smaller part of interest can then be enlarged whereby the image of the coronary tree volume data set, for example the model, is reduced in size. Of course, it is also possible to provide the different information on different displays that can be arranged according to the need of the actual situation or according to the user's needs.

According to the invention, in an exemplary embodiment, the object is also reached with an examination apparatus for reconstruction of the coronary arteries. The examination apparatus comprises at least one X-ray image acquisition device, a calculation unit, an electrocardiogram device and a display device. The electrocardiogram device is adapted for providing a gating signal. The image acquisition device is of a C-type and adapted for acquiring a first gated X-ray image sequence of one of the left and right branches of the coronary arteries with injected contrast agent into the one of the left or right branches of the coronary arteries and for acquiring a second gated X-ray image sequence of the other branch of the coronary arteries with injected contrast agent into said other branch. The calculation unit is adapted for performing gated reconstructions of the left and the right coronary artery and for generating volume data of the coronary arteries, for temporal registration of the volume data of the coronary arteries, for spatial registration of the volume data of the coronary arteries and for combining the volume data of the coronary arteries and generating the combined coronary artery tree volume data set. The display device is adapted for visualising the combined coronary tree volume data set image.

The examination apparatus provides the possibility of supplying a user with improved information about the current coronary artery situation, for example, of a patient. As the examination apparatus, according the invention, is capable of visualising a combined coronary tree volume data set image, the assessment of the coronary artery geometry is facilitated. This allows a quick and reliable diagnosis of the coronary situation. The combined coronary tree volume data set image, e.g. the model image, shows both sides of the artery tree at the same time of the cardiac cycle. In other words, as an effect of the invention, the artery branches shown on the generated image have the same relation as the investigated artery trees in reality.

Further exemplary embodiments of the apparatus are set forth in the dependent claims. The aspects and advantages discussed in relation to the exemplary embodiments of the method described above also apply to the exemplary embodiments of the apparatus, according to the invention, and vice versa.

The invention also provides an X-ray imaging system with an examination apparatus, according to the above mentioned embodiment, and according to the embodiments defined in the respective sub claims.

Thus, a system can be provided that supplies the user with improved information about the patient and that can also be used for other examination aspects related to the X-ray imaging system.

According to another exemplary embodiment of the present invention, a computer readable medium is provided, in which a computer program for reconstruction of the coronary arteries is stored which, when being executed by a processor, causes the processor to carry out the above mentioned method steps.

Furthermore, according to another exemplary embodiment of the present invention, a computer program element for reconstruction of the coronary arteries is provided which, when being executed by a processor, causes the processor to carry out the above mentioned method steps.

Those skilled in the art will readily appreciate that the method of reconstruction of the coronary arteries, according to the invention, may be embodied as a computer programme, i.e. by software, or may be embodied using one or more special electronic optimisation circuits, i.e. in hardware, or the method may be embodied in hybrid form, i.e. by means of software components and hardware components.

This exemplary embodiment of the invention covers both a computer program that right from the beginning uses the invention and a computer program that by means of an update turns an existing program into a program that uses the invention.

Further on, the computer program element might be able to provide all necessary steps to fulfil the procedure of the method as described above.

According to a further exemplary embodiment of the present invention, a medium for making a computer program element available for downloading is provided, which computer program element is arranged to perform the method, according to one of the previously described embodiments of the invention.

For example, existing imaging systems can be upgraded with a new software which, when being executed by a processor, causes the system to carry out the above mentioned method steps.

These and other aspects of the invention will be apparent from the exemplary embodiments described hereinafter with reference to the drawings.

DETAILED DESCRIPTION OF EMBODIMENTS

Figure 1:
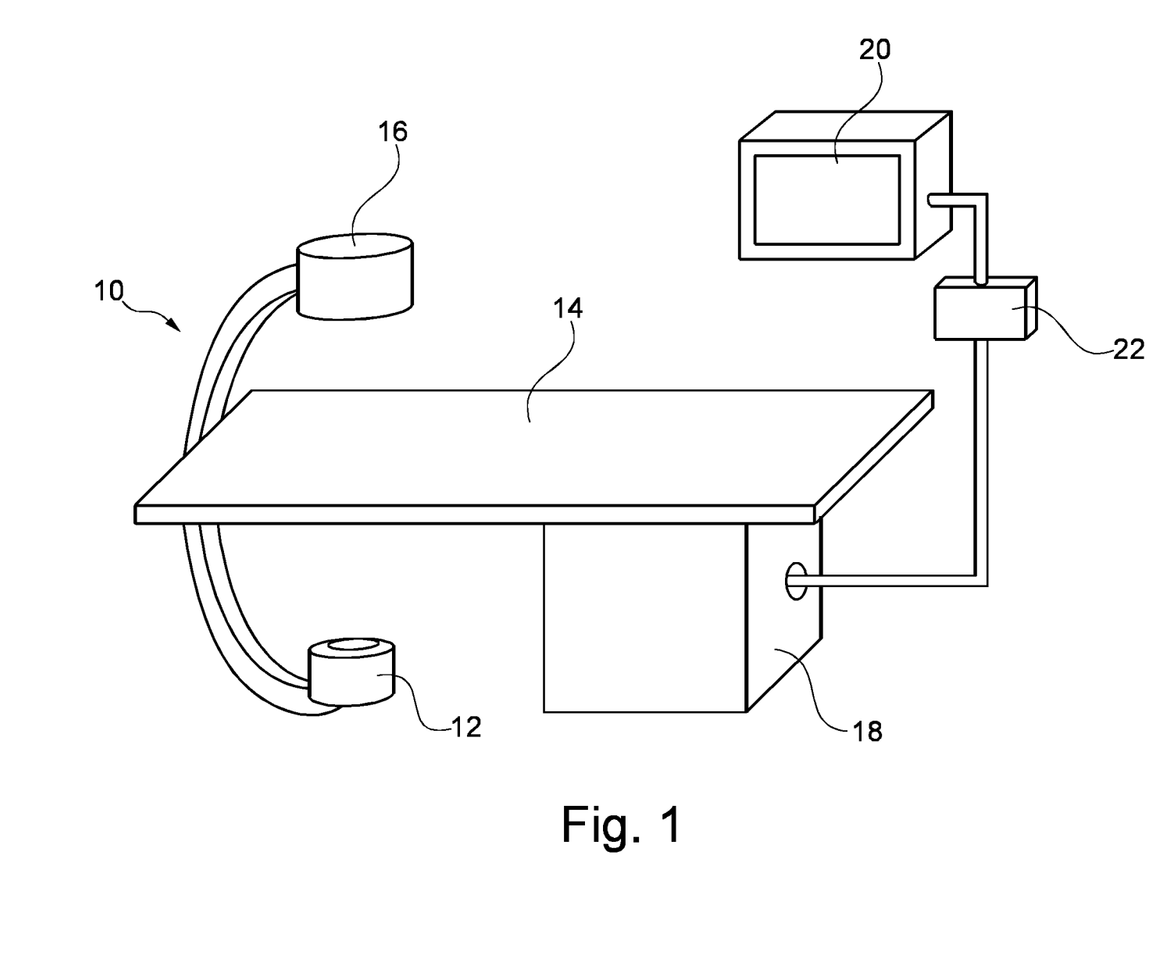
FIG. 1 shows an X-ray imaging system with an integrated examination apparatus for reconstruction of the coronary arteries, according to the invention.

FIG. 1 schematically shows an X-ray imaging system 10 with an examination apparatus for reconstruction of the coronary arteries. The examination apparatus comprises an X-ray image acquisition device with a source of X-ray radiation 12 provided to generate X-ray radiation. A table 14 is provided to receive a subject to be examined. Further, an X-ray image detection module 16 is located opposite the source of X-ray radiation 12, i.e. during the radiation procedure the subject is located between the source of X-ray radiation 12 and the detection module 16. The latter is sending data to a data processing unit or calculation unit 18, which is connected to both the detection module 16 and the radiation source 12. The calculation unit 18 is located underneath the table 14 to save space within the examination room. Of course, it could also be located at a different place, such as a different room or laboratory. Furthermore, a display device 20 is arranged in the vicinity of the table 14 to display information to the person operating the X-ray imaging system, which can be a clinician such as a cardiologist or cardiac surgeon. Preferably, the display device 20 is moveably mounted to allow for an individual adjustment depending on the examination situation. Also, an interface unit 22 is arranged to input information by the user. Basically, the image detection module 16 generates images by exposing the subject to X-ray radiation, wherein said images are further processed in the data processing unit 18. It is noted that the example shown is of a so-called C-type X-ray image acquisition device. The X-ray image acquisition device comprises an arm in form of a C where the image detection module 16 is arranged at one end of the C-arm and the source of X-ray radiation 12 is located at the opposite end of the C-arm. The C-arm is moveably mounted and can be rotated around the object of interest located on the table 14. In other words, it is possible to acquire images with different directions of view.

Figure 2:
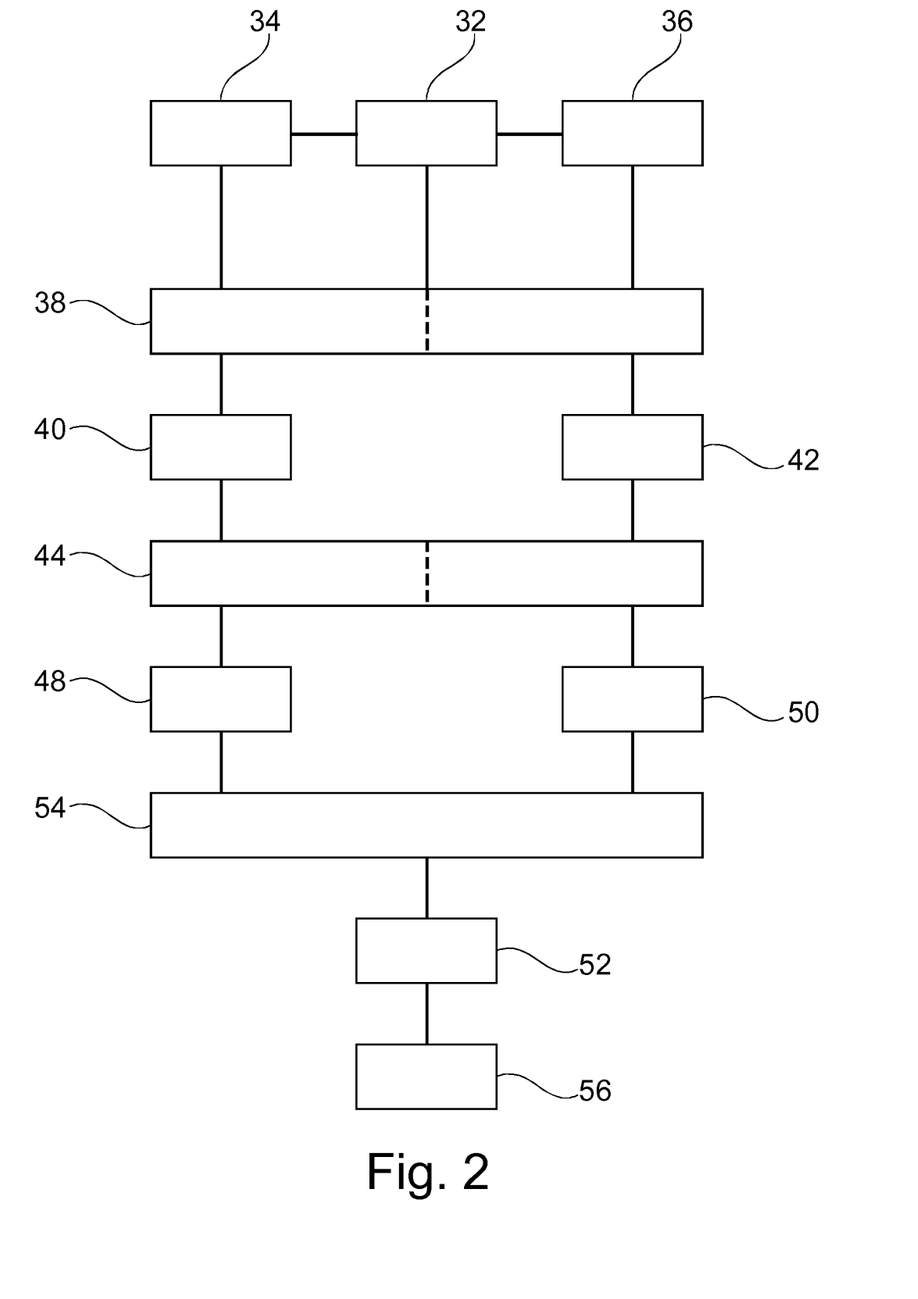
FIG. 2 schematically describes the method steps for reconstruction of the coronary arteries, according to the invention.

FIG. 2 schematically shows a flowchart of the steps, according to the invention. In a first step 32 a gating signal is provided for the following steps, for example, by an electrocardiogram. In a first acquiring procedure 34 a first gated X-ray image sequence of one of the left or right branches of the coronary arteries is acquired with injected contrast agent into the one of the left or right branches of the coronary arteries. In the exemplary embodiment in FIG. 2 the first acquiring step 34 is related to the left branch of the coronary artery.

In a second acquiring step 36 second gated X-ray image sequence of the other branch of the coronary arteries is acquired with injected contrast agent into said other branch. That means in the case shown in FIG. 2, the second acquiring step 36 is related to the right branch of the coronary arteries.

Following, the left and the right coronary arteries are reconstructed in a gated reconstructing step 38 and volume data of the coronary arteries is generated. As a result of step 38 a first volume data 40 of the left coronary artery and a second volume data of the right coronary artery are provided for the next steps. The first and second volume data 40, 42 of the left and right coronary arteries is registered in a spatial and time-relation registering step 44. The result of this step is a first registered volume data 48 of the left coronary artery and a second registered volume data 50 of the right coronary artery. In a next step the registered volume data 48, 50 are combined and a combined coronary artery tree volume data set 52 or model is generated in a combining and generation step 54. The combined coronary tree volume data set 52 is then visualised in a visualisation step 56.

In an exemplary embodiment, the first and second gated X-ray image sequences are rotational coronary angiography image sequences.

Figure 3:
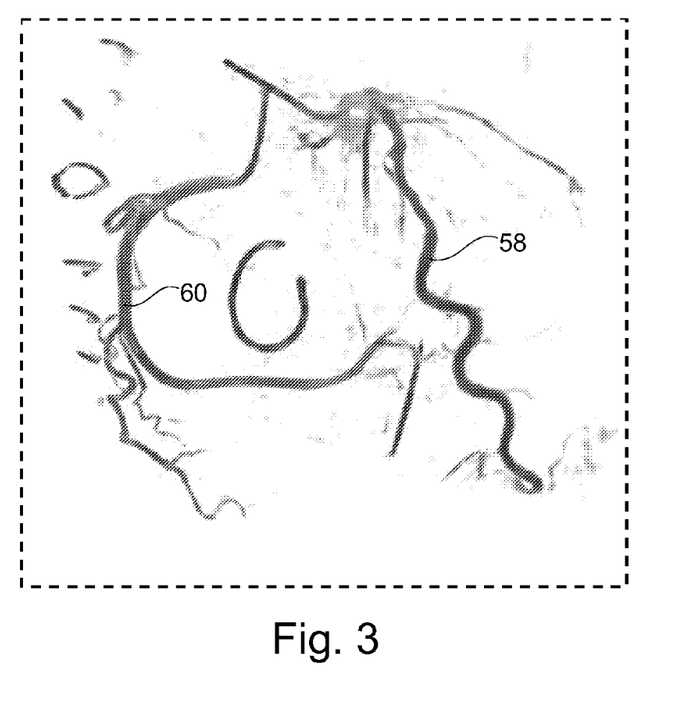
FIG. 3 shows a volume rendering of combined left and right coronary artery branches.

In FIG. 3 a result of the method steps shown in FIG. 2 is shown. The figure shows a volume rendering of a combined left coronary artery branch 58 and a right coronary artery branch 60.

Figure 4:
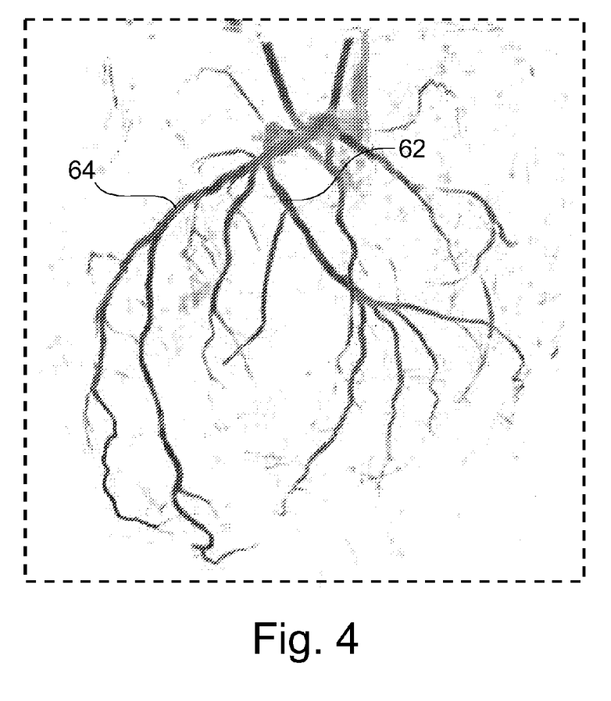
FIG. 4 shows another volume rendering of a combined coronary artery tree volume data set.

FIG. 4 shows another example for a combined coronary artery tree of a different object with a volume rendering of a combined left coronary artery branch 62 and a right coronary artery branch 64.

The images shown in FIGS. 3 and 4 provide a user, i.e., for example, a cardiologist, with detailed information about the coronary situation of the object of interest, i.e., for example, of a patient. Viewing the whole coronary artery tree potentially simplifies the assessment of the coronary artery geometry for the user. The left and right coronary arteries can be seen in direct relation to each other.

For further information an exemplary embodiment of the invention a combined coronary artery tree volume data set, e.g. a model, is generated for each cardiac phase, wherein each cardiac phase is temporally registered in relation to the gating signal.

Figure 5A:
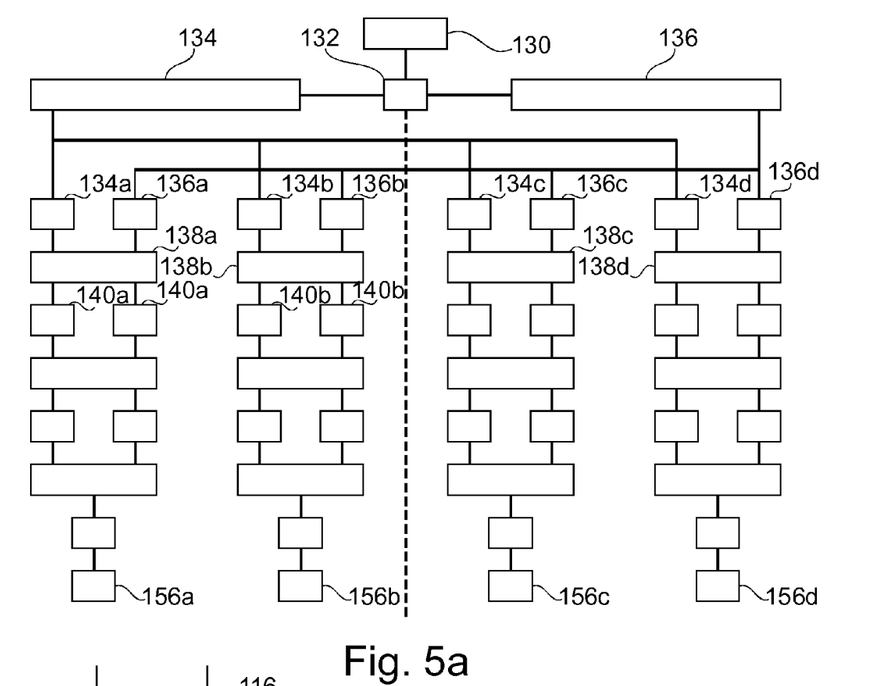
FIG. 5 shows the method steps for generating a combined artery tree volume data set for different cardiac phases.
Figure 5B:
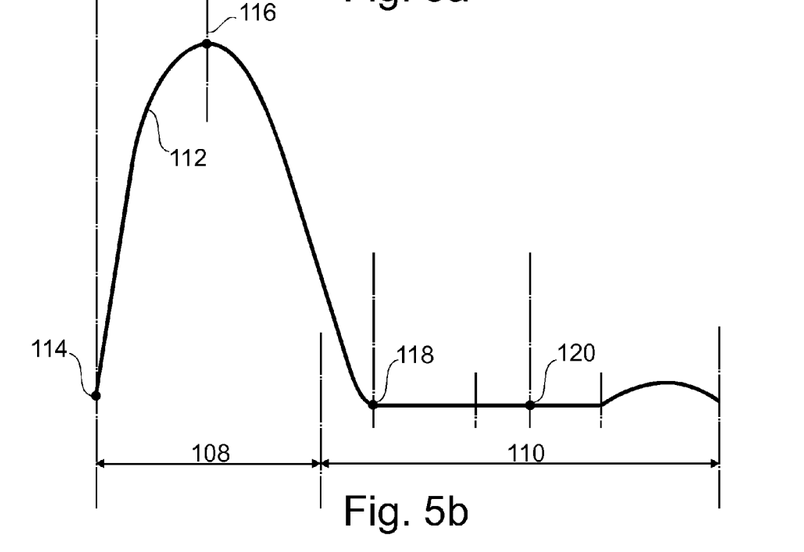

In FIG. 5 is shown an exemplary embodiment for a cardiac cycle with four different image phases relating to the cardiac cycle. The cardiac cycle is usually divided into a systole 108 and a diastole 110. As an example, the coronary artery situation should be examined for the beginning of the systole phase and the middle of the systole phase, i.e. where the aortic pressure reaches its maximum. In FIG. 5b) a pressure curve 112 is schematically shown. Along the curve 112, four different points are selected. A first point 114 for a first coronary artery tree volume data set is at the beginning of the systole phase 108. A second point 116 for a second coronary tree volume data set is at the climax of the curve 112. A third point 118 is at the beginning of the diastole phase 110. A fourth point 120 is set for the half of the diastole phase 110.

FIG. 5a) shows the steps based upon the above-mentioned cardiac cycle in FIG. 5b). First, as a gating signal 132, an electrocardiogram 130 is obtained from the patient. In an acquiring step 134 a first gated X-ray image sequence is acquired of the left branch of the coronary arteries with injected contrast agent into the left branch. In a second acquiring step 136 a second gated X-ray image sequence of the right branch of the coronary arteries is acquired with injected contrast agent into the right branch. By using the information of the gating signal 132 in relation to the cardiac phases 108, 110, or the cardiac cycle, shown below the flowchart, which information is achieved with the electrocardiogram 130 in respect of the four selected points 114, 116, 118, 120 of the cardiac cycle curve 112, four different sets of information 134a, 134b, 134c, 134d are provided for four different reconstructing steps 138a, 138b, 138c, 138d. In these reconstructing steps the left and the right coronary arteries are reconstructed in a gated manner and volume data 140a, 140b, 140c, 140d of the coronary arteries is generated.

The same applies to the second image sequence 136 where, according to the gating signal 132 and the information from the electrocardiogram 130, four different image data sets 136a, 136b, 136c, 136d are provided for the four different reconstructing steps 138a, 138b, 138c, 138d.

The following steps will be easily understood by reference to the description in relation with FIG. 2 and multiplying the step chains according to the four selected points in the cardiac cycle. Simply said, for generating a combined coronary artery tree volume data set or model for each cardiac phase, four procedures similar to that described in connection with FIG. 2 are accomplished. For example, the procedures can be carried out one after the other. For a faster result, it is also possible to carry out the procedures parallel to each other. However, as a result, four different combined coronary artery tree volume data sets 156a, b, c, d are achieved.

For example, the four different coronary artery tree volume data sets 156a, b, c, d can be shown as a film sequence on a display.

Figure 6A:
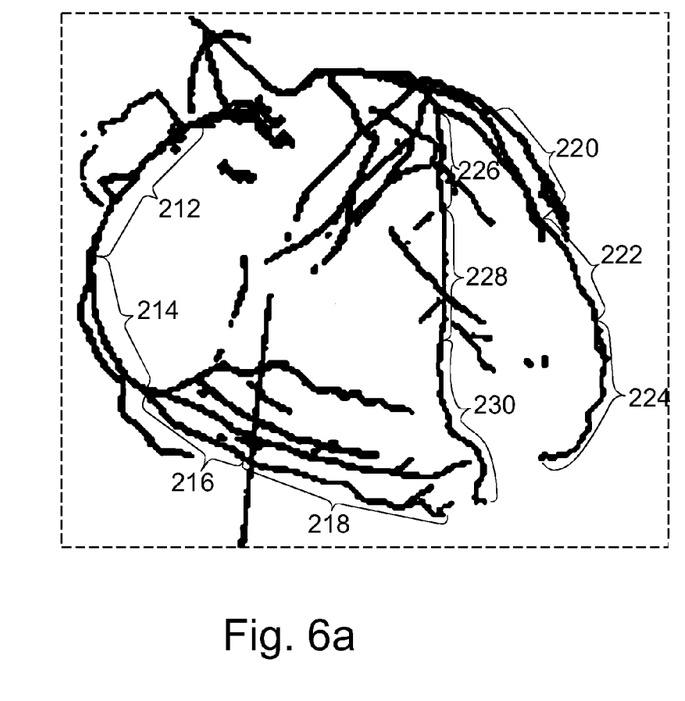
FIG. 6 shows maximum displacement amount of the coronary artery tree of FIG. 4.
Figure 6B:
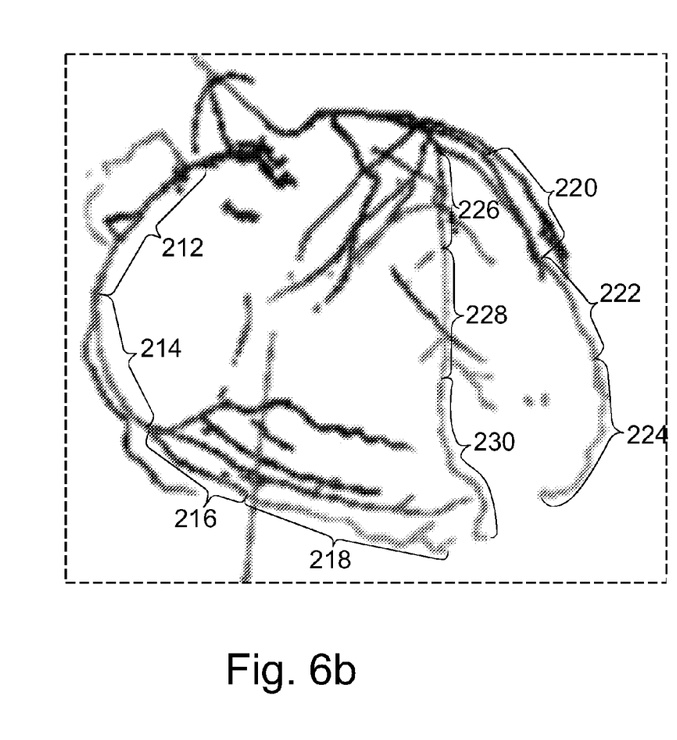

But the generated coronary artery tree film sequence comprising the four generated artery tree volume data sets 156a, b, c, d for each cardiac phase can also be used for further examination procedures. For example, they can be used for determining the displacement amount of the left and right arteries. The determined displacement values can then be converted into visual values. Visual values can be, for example, certain values of brightness or colour, respectively greyscale values. By providing the visual values, the displacement amount can be displayed on a display. As an example, FIG. 6 shows the maximum displacement of the right and left branches of the coronary arteries, where certain greyscale values represent certain displacement values. For example, on the left, a part 212 of right artery tree branch is having medium-high maximum displacement. Further, another part 214 downstream of the same branch has a high maximum displacement. Further on, another part 216 has a medium-high maximum displacement and a part 218 has a medium-low maximum displacement. The left branch on the right side of FIG. 6 is having a part 220 with a high maximum displacement, a part 222 with a medium-high and a part 224 with a medium-low maximum displacement. A further part 226 is showing a medium-high maximum displacement which is followed downstream from a medium-low part 228 and a low part 230.

By providing coronary artery tree volume data sets or models for each cardiac phase it is also possible to determine the speed of the displacement of the right and left arteries by relating the displacement values to time. The determined speed values can then be converted into visual values, i.e. values of brightness or colour values, respectively greyscale values. This can be used for displaying the speed occurrences on a display, which is exemplarily shown in FIG. 7.

Figure 7A:
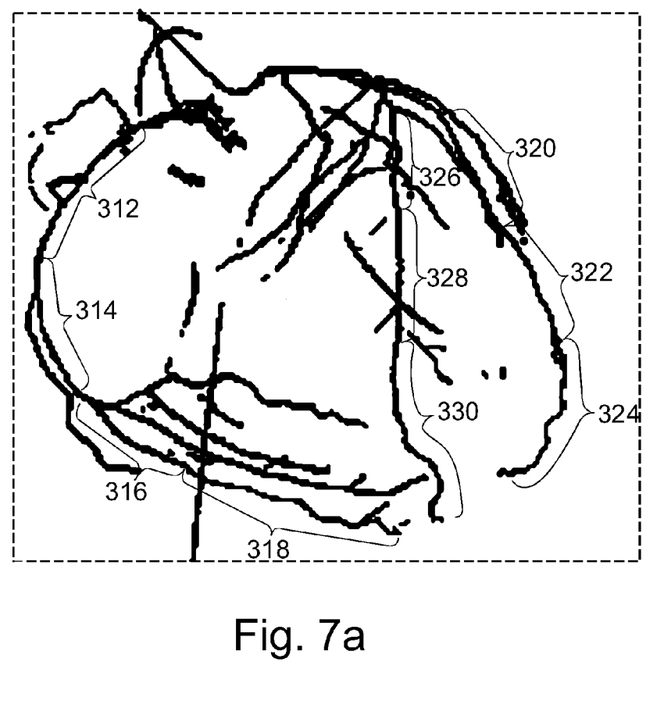
FIG. 7 shows the maximum displacement speed during the cardiac cycle of the coronary artery tree shown in FIG. 4.
Figure 7B:
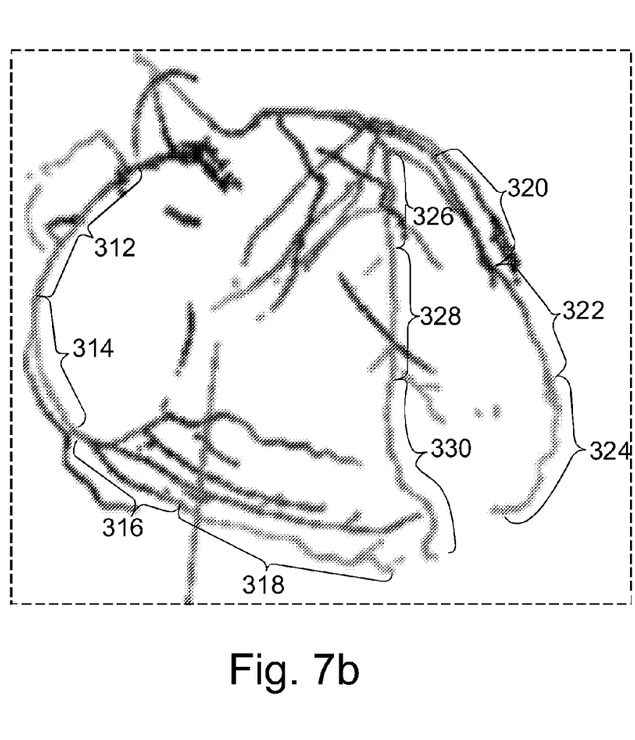

FIG. 7 shows the maximum speed values in certain greyscale values for the left and right branches of the coronary arteries. As an example, a first part 312 of one of the artery tree branches is having medium-high maximum speed. Another part 314 downstream of the branch has a high maximum speed. Further, another part 316 shows a medium-high maximum speed and a part 318 shows a medium-low maximum speed. The other branch on the right side of FIG. 7 is having a part 320 with a high maximum speed value and a part 322 with a medium-high and a part 324 with a medium-low maximum speed value. Further, another part 326 is showing a medium-high maximum speed which is followed downstream from a medium-low part 328 and a part 330 with low maximum speed.

Thus, the information shown in FIGS. 6 and 7 is providing dynamic information about the heart motion to the user, which allows for a more detailed and precise diagnosis.

The information obtained by using coronary tree volume data sets, respectively models, for different cardiac phases can also be used for automatic detecting abnormal motion, for example. This is because the displacement of the left and right arteries can be determined in relation to each other. The displacement can then be compared with preset displacement values. Based upon this comparison, display information can be generated and displaced to the user. This provides quick and easily accessible information about potential abnormalities in the heart motion without the need of thoroughly studying displacement or maximum speed values.

While the invention has been illustrated and described in detail in the drawings and foregoing description, such illustration and description are to be considered illustrative or exemplary and not restrictive; the invention is not limited to the disclosed embodiments.

The invention claimed is:

1. An examination apparatus for reconstruction of the coronary arteries, the examination apparatus comprising:
   an X-ray image acquisition device;
   an X-ray image reconstruction processor;
   an electrocardiogram device; and
   a display device;
   wherein the electrocardiogram device is configured for providing a gating signal;
   wherein the image acquisition device is configured for acquiring a first gated X-ray image sequence of one of the left and right branches of the coronary arteries with injected contrast agent into the one of the left or right branches of the coronary arteries and for acquiring a second gated X-ray image sequence of the other branch of the coronary arteries with injected contrast agent into said other branch;
   wherein said processor is configured:
      for performing gated reconstructions of the left and the right coronary artery and for generating volume data of the coronary arteries;
      for temporal registration of the volume data of the coronary arteries;
      for spatial registration of the volume data of the coronary arteries; and for combining the volume data of the coronary arteries and generating a combined coronary artery tree volume data set; and wherein said apparatus is configured for, via said display device, visualizing the combined coronary tree volume data set image.

2. The apparatus according to claim 1, wherein the image acquisition device is configured for generating combined coronary artery tree volume data sets for each cardiac phase; and wherein said processor is configured for generating at least one combined coronary artery tree film sequence.

3. The apparatus according to claim 1, wherein said processor is configured:

for determining a displacement amount of each of the left and right arteries; and for converting the determined displacement amounts into visual values, said apparatus being configured for, via said display device, displaying the displacement amounts.

4. The apparatus according to claim 1, wherein said processor is configured:

for determining a speed of the displacement of each of the left and right arteries by relating respective displacement amounts to time; and for converting the determined speed values into visual values, said apparatus being configured for, via said display device, displaying speed occurrences.

5. An X-ray imaging system comprising an apparatus according to claim 1 and a source of X-ray radiation for irradiating said X-ray image acquisition device.

6. The examination apparatus of claim 1, the generated volume data comprising first volume data of the left coronary artery and second volume data of the right coronary artery, said combining operating on both a set of data derived from said first volume data and a set of data derived from said second volume data.

7. The examination apparatus of claim 6, wherein said image acquisition device comprises an X-ray source, an X-ray detector, and a C-shaped structure that physically connects said source and said detector.

8. The examination apparatus of claim 1, wherein said image acquisition device comprises an X-ray source, an X-ray detector, and a C-shaped structure that physically connects said source and said detector.

9. The examination apparatus of claim 1, said temporal and said spatial registration being performed between a portion of said volume data of the left coronary artery and a portion of said volume data of the right coronary artery, said portions having been generated by respective reconstructions that are gated to a same cardiac phase.

10. The examination apparatus of claim 9, configured for said temporal and said spatial registrations between portions, and said respective reconstructions, for each of a plurality of cardiac phases, and for generating a coronary artery tree film sequence based on a plurality of different combined coronary artery tree volume data sets of respective cardiac phases, said combined coronary artery tree volume data set being among said plurality of different sets.

11. The apparatus of claim 1, further configured for:

for each cardiac phase, both said generating and said visualizing; and temporally registering each cardiac phase in relation to said gating signal.

12. A method for reconstruction of the coronary arteries, the method comprising the steps of:

providing a gating signal;

acquiring a first gated X-ray image sequence of one of the left or right branches of the coronary arteries with injected contrast agent into the one of the left or right branches of the coronary arteries;

acquiring a second gated X-ray image sequence of the other branch of the coronary arteries with injected contrast agent into said other branch;

gated reconstructing of the left and the right coronary artery and generating volume data of the coronary arteries;

temporal registering of the volume data of the left and right coronary arteries;

spatial registering of the volume data of the left and right coronary arteries;

combining the registered volume data of the left and the right coronary artery and generating a combined coronary artery tree volume data set; and visualizing the combined coronary tree volume data set.

13. The method according to claim 12, wherein the first and the second gated X-ray image sequences are rotational coronary angiography image sequences.

14. The method according to claim 12, wherein the reconstruction is a tomographical reconstruction.

15. The method according to claim 12, comprising generating a combined coronary artery tree volume data set for each cardiac phase; wherein each cardiac phase is temporally registered in relation to the gating signal.

16. The method according to claim 15, comprising generating at least one combined coronary artery tree film sequence.

17. The method according to claim 16, comprising: determining a displacement amount of each of the left and right arteries; converting the determined displacement amounts into visual values; and displaying the displacement amounts.

18. The method according to claim 17, comprising: determining a speed of the displacement of each of the left and right arteries by relating the respective displacement amounts to time; converting the determined speed values into visual values; and displaying speed occurrences.

19. The method according to claim 17, comprising: determining the displacement amounts of the left and right arteries in relation to each other; comparing the displacement amounts with pre-set displacement values; and generating and displaying displacement information.

20. A non-transitory computer readable medium embodying a computer program for reconstructing coronary arteries, said program comprising instructions executable by a processor to perform a plurality of acts, from among said plurality there being the acts of:

providing a gating signal;

acquiring a first gated X-ray image sequence of one of the left or right branches of the coronary arteries with injected contrast agent into the one of the left or right branches of the coronary arteries;

acquiring a second gated X-ray image sequence of the other branch of the coronary arteries with injected contrast agent into said other branch;

gated reconstructing of the left and the right coronary artery and generating volume data of the coronary arteries;

temporal registering of the volume data of the left and right coronary arteries;

spatial registering of the volume data of the left and right coronary arteries;

combining the registered volume data of the left and the right coronary artery and generating a combined coronary artery tree volume data set; and visualizing the combined coronary tree volume data set.

21. The computer readable medium of claim 20, said temporal and said spatial registering being performed between a portion of said volume data of the left coronary artery and a portion of said volume data of the right coronary artery, said portions having been generated by respective reconstructing that is gated to a same cardiac phase.

22. The computer readable medium of claim 21, from among said plurality of acts there being the acts of:

said temporal and said spatial registering between respective portions, and said respective reconstructing, for each of a plurality of cardiac phases, said same cardiac phase being among said plurality of cardiac phases; and generating a coronary artery tree film sequence based on a plurality of different combined coronary artery tree volume data sets of respective ones of the plural cardiac phases, said combined coronary artery tree volume data set being among said plurality of different sets.

23. The computer readable medium of claim 22, from among said plurality of acts there being the act of:

showing, as said film sequence, said plurality of different sets.

* * * * *